United States Patent [19]
Wu et al.

[11] Patent Number: 6,160,145
[45] Date of Patent: Dec. 12, 2000

[54] TRANSITION METAL COMPOUNDS HAVING CONJUGATE ALUMINOXATE ANIONS AND THEIR USE AS CATALYST COMPONENTS

[75] Inventors: Feng-Jung Wu; Jamie R. Strickler, both of Baton Rouge, La.

[73] Assignee: Albemarle Corporation, Richmond, Va.

[21] Appl. No.: 09/177,736

[22] Filed: Oct. 23, 1998

[51] Int. Cl.[7] .............................. C07F 17/00; C07F 19/00; C07F 5/06; C07F 7/00

[52] U.S. Cl. ................................ 556/27; 556/11; 556/12; 556/28; 526/127; 526/160; 526/943; 502/103; 502/117; 502/153

[58] Field of Search .................................. 556/27, 28, 11, 556/12; 526/127, 160, 943; 502/103, 117, 153

[56] References Cited

U.S. PATENT DOCUMENTS

| | | | |
|---|---|---|---|
| 4,658,078 | 4/1987 | Slaugh et al. | 585/512 |
| 4,752,597 | 6/1988 | Turner | 502/104 |
| 4,814,540 | 3/1989 | Watanabe et al. | 585/523 |
| 4,960,878 | 10/1990 | Crapo et al. | 556/179 |
| 5,008,228 | 4/1991 | Chang | 502/111 |
| 5,041,584 | 8/1991 | Crapo et al. | 556/179 |
| 5,087,788 | 2/1992 | Wu | 585/512 |
| 5,126,303 | 6/1992 | Resconi et al. | 502/117 |
| 5,145,819 | 9/1992 | Winter et al. | 502/117 |
| 5,147,949 | 9/1992 | Chang | 526/129 |
| 5,153,157 | 10/1992 | Hlatky et al. | 502/117 |
| 5,198,401 | 3/1993 | Turner et al. | 502/155 |
| 5,241,025 | 8/1993 | Hlatky et al. | 526/129 |
| 5,296,433 | 3/1994 | Siedle et al. | 502/117 |
| 5,321,107 | 6/1994 | Tsutsui et al. | 526/138 |
| 5,324,800 | 6/1994 | Welborn, Jr. et al. | 526/160 |
| 5,340,786 | 8/1994 | Tsutsui et al. | 502/117 |
| 5,374,753 | 12/1994 | Yamada et al. | 556/11 |
| 5,384,299 | 1/1995 | Turner et al. | 502/155 |
| 5,391,629 | 2/1995 | Turner et al. | 525/268 |
| 5,408,017 | 4/1995 | Turner et al. | 526/134 |
| 5,502,017 | 3/1996 | Marks et al. | 502/103 |
| 5,539,068 | 7/1996 | Devore et al. | 526/126 |
| 5,565,533 | 10/1996 | Galimberti et al. | 526/127 |
| 5,599,761 | 2/1997 | Turner | 502/152 |
| 5,621,126 | 4/1997 | Canich et al. | 556/9 |
| 5,693,727 | 12/1997 | Goode et al. | 526/86 |
| 5,712,352 | 1/1998 | Brant et al. | 526/68 |
| 5,854,166 | 12/1998 | Marks et al. | 502/103 |

FOREIGN PATENT DOCUMENTS

| | | |
|---|---|---|
| 0277003 | 8/1988 | European Pat. Off. . |
| 0277004 | 8/1988 | European Pat. Off. . |
| 0816399 | 7/1998 | European Pat. Off. . |
| 2010468 | of 1970 | France . |
| 2608863 | 9/1977 | Germany . |
| 2608933 | 9/1977 | Germany . |
| 3240382 | 5/1984 | Germany . |
| 9602580 | 2/1996 | WIPO . |
| 9832776 | 7/1998 | WIPO . |

OTHER PUBLICATIONS

Kaminsky, Walter, "New Polymers by Metallocene Catalysis", Macromolecular Chemistry Phys., 1996, vol. 197, pp. 3907–3945.

Bochmann, Manfred "Cationic Group 4 metallocene complexes and their role in polymerisation catalysis: the chemistry of well defined Ziegler catalysts", J. of the Chem. Soc.,Dalton Trans., 1996, vol. 3, pp. 255–270.

Boleslawski, M. et al., "Investigations of The Hydrolysis Reaction Mechanism of Organoaluminium Compounds, $^1$H NMR Spectroscopic Studies on the $R_3Al/H_2O$ Reaction In Polar Solvents", Journal of Organometallic Chem. vol. 255, 1983, pp. 269–278.

Harlan Jeff C. et al., tert–Butylaluminum Hydroxides and Oxides: Structural Relationship between Alkylalumoxanes and Alumina Gels, Organometallics vol. 13, 1994, pp. 2957–2969.

Harlan et al., "Three–Coordinate Aluminum Is Not a Prerequisite for Catalytic Activity in the Zirconocene–Alumoxane Polymerization of Ethylene" J. Am. Chem. Soc. 1995, vol. 117, pp. 6465–6474.

Jia et al., "Protected (Fluoroaryl)borates as Effective Counteranions for Cationic Metallocene Polymerization Catalysts", Organometallics 1995 vol. 14, pp. 3135–3137.

Johnson et al., "New Pd(II)– and Ni(II)–Based Catalysts for Polymerization of Ethylene and α–Olefins", J. Am. Chem. Soc. 1995, vol. 117, pp. 6414–6415.

Kaminsky, Dr. W., "Metallocene Catalysts", SP'92–Polyethylene World Congress, Dec. 1992, 12 pages.

Killian et al., "Living Polymerization of α–Olefins Using $Ni^{11}$–α–Diimine Catalysts. Synthesis of New Block Polymers Based on α–Olefins", J. Am. Chem. Soc. 1996, vol. 118, pp. 11664–11665.

Landry et al., "Galloxane and Alumoxane Hydroxides: $[Ga_{12}\tau Bu_{12}(\mu_3-O)_8(\mu-O)_2(\mu-OH)_4]$ and $[Al_6tBu_6(\mu_3-O)_4(\mu-OH)_4]$" Angew. Chem. Int. Ed. Engl., 1995, vol. 34, No. 11, pp.1201–1202.

Mason, et al., "Hydrolysis of Tri–tert–butylaluminum: The First Structrual Characterization of Alkylalumoxanes $[(R_2Al)_2O]_n$ and $(RalO)_n$", J. Am. Chem. Soc., 1993, vol. 115, pp. 4971–4984.

(List continued on next page.)

*Primary Examiner*—Porfirio Nazario-Gonzalez
*Attorney, Agent, or Firm*—Philip M. Pippenger

[57] ABSTRACT

Novel, highly effective catalyst compositions are described in which a low cost co-catalyst can be employed at very low aluminum loadings. Such compounds are composed of a cation derived from d-block or f-block metal compound, such as a metallocene, by loss of a leaving group, and an aluminoxate anion derived by transfer of a proton from a stable or metastable hydroxyaluminoxane to such leaving group. These catalyst compositions have extememly high catalytic activity and typically have high solubility in paraffinic solvents. Moreover they yield reduced levels of ash and result in improved clarity in polymers formed from such catalysts.

39 Claims, 5 Drawing Sheets

OTHER PUBLICATIONS

Pieters, et al., "A Method for the Prediction of Metallocene-Type Catalyst Activity in Olefin (co)polymerisation reactions", Macromol Rapid Commun., vol. 16, 1995, pp. 463–467.

Samuel, E. et al., "π–Cyclopentadienyl and π–Indenyl Compounds of Titanium, Zirconium, and Hafnium Containing o–Bonded Organic Substituents[1]", J. Of the Am. Chem. Soc., 1973, vol. 95, pp. 6263–6267.

Small, Brooke L. et al., "Highly Active Iron and Cobalt Catalysts for the Polymerization of Ethylene", J. Am. Chem. Soc., 1998, vol. 120, pp. 4049–4050.

Spaleck, Walter et al., "High Molecular Weight Polypropylene through Specifically Designed Zirconocene Catalysts", Angew. Chem. Int. ED. Engl. 1992, vol. 31, No. 10, pp. 1347–1350.

Storre, Jens et al., "Hydrolysis of Trimesitylgallium and Trimesitylaluminum: Structures Along a Reaction Pathway", J. Am. Chem. Soc., 1996, vol. 118 pp. 1380–1386.

Storre, Jens et al., "A Novel Approach For the Stabilization & Structural Characterization of Group 13 Organometallic Hydroxides: The Way to Well Defined Crystalline Methylalumoxanes", J. Am. Chem. Soc., vol. 119, No. 32, 1997, pp. 7505–7513.

Siedle, A.R. et al, "How Coordinating Are Non–Coordinating Anions?", Macromol. Symp. vol. 89, 1995, pp. 299–305.

Veith, Michael et al., "An $Al_4(OH)_4$ Eight–Membered Ring in a Molecular Aluminopolysiloxane and Its Behavior with Bases", Angew, Chem. Int. Ed. Engl. 1997, vol. 36, No. ½, pp. 117–119.

Chen, You–Xian et al., "Very Large Counteranion Modulation of Cationic Metallocene Polymerization Activity and Steroregulation by a Sterically Congested (Perfluoroaryl)fluoroaluminate", J. Am. Chem. Soc., vol. 119, No. 10, 1997, pp. 2582–2583.

Brintzinger, Hans H. et al, "Sterospecific Olefin Polymerization with Chiral Metallocene Catalysts", Angew. Chem. Int. Ed Engl., 1995, vol. 34, pp. 1143–1170.

Hlatky, Gregory G. et al., "Ionic, Base–Free Zirconocene Catalysts for Ethylene Polymerization", J. Am. Chem. Soc. 1989, vol. 111, pp. 2728–2729.

Hlatky, Gregory G. et al., "Supported Ionic Metallocene Polymerization Catalysts", Macromolecules, 1996, vol. pp. 8019–8020.

Ikonitski, I.V. et al., "IR Spectroscopic Study of the Formation of a Complex Alkylalumoxane Catalyst for The Polymerization of α–Oxides of Olefins", pp. 351–354, Translated from Zhurnal Prikladnoi Khimii, vol. 62, No. 2 pp. 394–397, Feb., 1989.

TRANSITION METAL COMPOUNDS HAVING CONJUGATE ALUMINOXATE ANIONS AND THEIR USE AS CATALYST COMPONENTS

TECHNICAL FIELD

This invention relates to novel compositions of matter which are highly effective as catalyst components, and to the preparation and use of such compositions.

BACKGROUND

Partially hydrolyzed aluminum alkyl compounds known as aluminoxanes (a.k.a. alumoxanes) are effective in activating metallocenes for polymerization of olefins. Activating effects of water in such systems were initially noted by Reichert, et al. (1973) and Breslow, et al. (1975), and extended to trimethylaluminum-based systems by Sinn, Kaminsky, et al. (1976). Subsequent research by Sinn and Kaminsky demonstrated that this activation was due to formation of methylaluminoxane from partial hydrolysis of trimethylaluminum present in the system. Methylaluminoxane (a.k.a. methylalumoxane) has become the aluminum co-catalyst of choice in the industry.

Subsequent to the above original discoveries in this field, considerable worldwide effort has been devoted to improving the effectiveness of catalyst systems based on use of aluminoxanes or modified aluminoxanes for polymerization of olefins and related unsaturated monomers.

Representative of many patents in the field of aluminoxane usage in forming olefin polymerization catalyst systems with suitable metal compounds is U.S. Pat. No. 5,324,800 to Welborn et al. which claims an original filing date in 1983. This patent describes olefin polymerization catalysts made from metallocenes of a metal of Groups 4b, 5b, or 6b, and a cyclic or linear $C_1$–$C_5$ alkylaluminoxane. The cyclic and the linear aluminoxanes are depicted, respectively, by the formulas (R—Al—O)$_n$ and R(R—Al—O)$_n$AlR$_2$ where n is from 1 to about 20, and R is most preferably methyl. The aluminoxanes are made by controlled hydrolysis of the corresponding aluminum trialkyl.

Another relatively early patent in the field, U.S. Pat. No. 4,752,597 to Turner based on a filing date of 1985, describes olefin polymerization catalysts comprising the reaction products of a metallocene complex of group IVB, VB, VIB, and VIII of the periodic table and an excess of aluminoxane. These catalysts are formed by pre-reacting a metallocene and an aluminoxane in mole ratios greater than 12:1, such as about 12:1 to about 100:1, to produce a solid product which precipitates from solution. Despite assertions of suitable catalytic activity, in reality the activity of these materials is so low as to be of no practical importance whatsoever.

In U.S. Pat. Nos. 4,960,878 and 5,041,584 to Crapo et al. modified methylaluminoxane is formed in several ways. One involves reacting a tetraalkyldialuminoxane, $R_2$Al—O—AlR$_2$, containing $C_2$ or higher alkyl groups with trimethylaluminum (TMA) at −10 to 150° C. Another involves reacting TMA with a polyalkylaluminoxane (—Al(R)—O—)$_n$ where R is $C_2$ alkyl or higher and n is greater than 1, e.g., up to 50. Temperatures suggested for this reaction are −20 to 50° C. A third way involves conducting the latter reaction and then reacting the resultant product, which is indicated to be a complex between trimethylaluminum and the polyalkylaluminoxane, with water. The patent states that the water-to-aluminum ratios used to make the polyalkylaluminoxane reagent have an effect on the activity of the final methylaluminoxane. On the basis of ethylene polymerizations using zirconocene dichloride catalyst and a complex of trimethylaluminum with polyisobutylaluminoxane subsequently reacted with water (MMAO) as co-catalyst, it is indicated in the patent that the highest polymerization activities were achieved with MMAO co-catalyst prepared at $H_2$O/Al ratios of about 0.6 to about 1.0 and Al/Zr ratios in the range of 10,000/1 to 400,000/1.

Various references are available indicating that isobutylaluminoxanes themselves are relatively ineffective on their own as co-catalysts. For example, several other reactions of alkylaluminum compounds with water are disclosed in U.S. Pat. Nos. 4,960,878 and 5,041,584. Thus in Example 1 of these patents, DIBAL-O (tetraisobutyldialuminoxane), a commercial product, was prepared by reaction of water with triisobutylaluminum (TIBA) in heptane using a water/TIBA ratio of about 0.5, followed by solvent stripping at 58–65° C. under vacuum. In Examples 3–6 of the patents isobutylaluminoxane (IBAO) was prepared by controlled addition of water to a 25% solution of TIBA in toluene in the temperature range of 0–12° C., followed by heating to 70–80° C. to ensure complete reaction and remove dissolved isobutane. $H_2$O/Al ratios used were 0.98, 1.21, 1.14, and 0.88. IBAO was again made in a similar manner in Example 52 of the patents. Here the $H_2$O/Al ratio was 0.70, and the product was heated at 75° C. And in Example 70 tri-n-butylaluminum (TNBA) in toluene was treated at 0–10° C. with water followed by heating to 85° C. Ethylene polymerizations using zirconocene dichloride catalyst and various products from the foregoing Examples were conducted. Specific activities ($\times 10^3$ gPE/(gZr.atm $C_2H_4$.hr)) of the catalysts made with DIBAL-O from Ex. 1, IBAO from Ex. 3, and IBAO from Ex. 6 were, respectively, 4.1, 4.2, and 7.7, as compared to 1000 for the catalyst made using conventional MAO as the co-catalyst. The patents acknowledge that tetraisobutyldialuminoxane (DIBAL-O) showed "poor polymerization activity", and from the foregoing test results the same can be said to apply to IBAO.

WO 96/02580 to Dall'occo, et al. describes olefin polymerization catalysts made by contacting a metallocene of Ti, Zr, or Hf, an organoaluminum compound having at least one specified hydrocarbon substituent on the β-carbon atom of an aliphatic group bonded to an aluminum atom, and water. Various ways of bringing these components together are suggested. Polymerizations described were carried out using Al/Zr mole ratios ranging from 500 up to as high as 5000.

EP 0 277 004 to Turner, published in 1988, describes the successful preparation and use as catalysts composed of an ionic pair derived from certain metallocenes of Group 4, most preferably bis(cyclopentadienyl)zirconium dimethyl or bis(cyclopentadienyl)hafnium dimethyl, reacted with certain trisubstituted ammonium salts of a substituted or unsubstituted aromatic boron compound, most preferably N,N-dimethylanilinium tetra(pentafluorophenyl)boron. While EP 0 277 004 mentions that compounds containing an element of Groups V-B, VI-B, VII-B, VIII, I-B, II-B, III-A, IV-A, and V-A may be used in forming the catalysts, no specific compounds other than boron compounds are identified. In fact, EP 0 277 004 appears to acknowledge inability to identify specific compounds other than boron compounds by stating: "Similar lists of suitable compounds containing other metals and metalloids which are useful as second components could be made, but such lists are not deemed necessary to a complete disclosure." See in this connection Hlatky, Turner and Eckman, *J. Am. Chem. Soc.*, 1989, 111, 2728–2729, and Hlatky and Upton, *Macromolecules*, 1996, 29, 8019–8020.

U.S. Pat. No. 5,153,157 to Hlatky and Turner states that its process "is practiced with that class of ionic catalysts referred to, disclosed, and described in European Patent Applications 277,003 and 277,004." The process of U.S. Pat. No. 5,153,157 involves forming an ionic catalyst system from two components. The first is a bis(cyclopentadienyl) derivative of a Group IV-B metal compound containing at least one ligand which will combine with the second component or portion thereof such as a cation portion thereof. The second component is referred to as an ion exchange compound comprising (1) a cation which will irreversibly react with a ligand of the Group IV-B metal compound and (2) a noncoordinating anion which is bulky, labile, and stable. The second component, also termed an activator component, comprises compounds of Groups V-B, VI-B, VII-B, VIII, I-B, II-B, III-A, IV-A, and V-A identified by a general formula. Besides referring to the boron compounds of EP 277,004, supra, such as tri(n-butylammonium)tetra (pentafluorophenyl)boron and N,N-dimethylanilinium tetra (pentafluorophenyl)boron as suitable activators, the U.S. '157 patent teaches use of boron compounds having a plurality of boron atoms, and also trialkyl aluminum compounds, triaryl aluminum compounds, dialkylaluminum alkoxides, diarylaluminum alkoxides, and analogous compounds of boron. Of the organoaluminum activators triethylaluminum and trimethylaluminum are specified as most preferred. The Examples show use of a catalyst system formed from (1) a solution of bis(cyclopentadienyl) zirconium dimethyl or bis(cyclopentadienyl)hafnium dimethyl and N,N-dimethylanilinium tetra(pentafluorophenyl) boron together with (2) triethylborane, triethylaluminum, tri-sec-butylborane, trimethylaluminum, and diethylaluminum ethoxide. In some cases the catalyst formed from the metallocene and the N,N-dimethylanilinium tetra (pentafluorophenyl)boron without use of a compound of (2) gave no polymer at all under the polymerization conditions used.

U.S. Pat. No. 5,198,401 to Turner, Hlatky, and Eckman refers, in part, to forming catalyst compositions derived from certain metallocenes of Group 4, such as bis (cyclopentadienyl)zirconium dimethyl or bis (cyclopentadienyl)hafnium dimethyl, reacted with certain trisubstituted ammonium salts of a substituted or unsubstituted aromatic boron compound, such as N,N-dimethylanilinium tetra(pentafluorophenyl)boron or tributylammonium tetra(pentafluorophenyl)boron as in EP 0 277 004. However here the anion is described as being any stable and bulky anionic complex having the following molecular attributes: 1) the anion should have a molecular diameter about or greater than 4 angstroms; 2) the anion should form stable salts with reducible Lewis acids and protonated Lewis bases; 3) the negative charge on the anion should be delocalized over the framework of the anion or be localized within the core of the anion; 4) the anion should be a relatively poor nucleophile; and 5) the anion should not be a powerful reducing or oxidizing agent. Anions of this type are identified as polynuclear boranes, carboranes, metallacarboranes, polyoxoanions and anionic coordination complexes. Elsewhere in the patent it is indicated that any metal or metalloid capable of forming a coordination complex which is resistant to degradation by water (or other Brønsted or Lewis acids) may be used or contained in the second activator compound [the first activator compound appears not to be disclosed]. Suitable metals of the second activator compound are stated to include, but not be limited to, aluminum, gold, platinum and the like. No such compound is identified. Again after listing boron compounds the statement is made that "Similar lists of suitable compounds containing other metals and metalloids which are useful as second components could be made, but such lists are not deemed necessary to a complete disclosure." In this connection, again note Hlatky, Turner and Eckman, *J. Am. Chem. Soc.*, 1989, 111, 2728–2729, and Hlatky and Upton, *Macromolecules*, 1996, 29, 8019–8020.

Despite the above and many other efforts involving aluminum co-catalysts, the fact remains that in order to achieve suitable catalysis on a commercial basis, relatively high aluminum to transition metal ratios must be employed. Typically for optimal activity an aluminum to metallocene ratio of greater than about 1000:1 is required for effective homogeneous olefin polymerization. According to Brintzinger, et al., *Angew. Chem. Int. Ed. Engl.*, 1995, 34 1143–1170:

"Catalytic activities are found to decline dramatically for MAO concentrations below Al:Zr ratio roughly 200–300:1. Even at Al:Zr ratios greater than 1000:1 steady state activities increase with rising MAO concentrations approximately as the cube root of the MAO concentration".

This requirement of high aluminum loading is mainly caused by a metallocene activation mechanism in which generation of catalytically active species is equilibrium driven. In this role MAO acts as a Lewis acid to remove by group transfer a leaving group $X^\ominus$ from the transition metal. This forms a weakly-coordinating anion, MAO-$X^\ominus$, in the corresponding transition metal cation. That is, in such systems the following equilibrium exists:

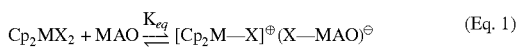

$$Cp_2MX_2 + MAO \underset{}{\overset{K_{eq}}{\rightleftharpoons}} [Cp_2M\text{---}X]^\oplus(X\text{---}MAO)^\ominus \qquad \text{(Eq. 1)}$$

The Lewis acid sites in MAO abstract a negatively charged leaving group such as a methide group from the metallocene to form the catalytically active ion pair. The activation process is reversible and $K_{eq}$ is typically small. Thus the ion pair can return to its neutral precursors which are catalytically inactive. To overcome this effect, a large excess of MAO is required to drive the equilibrium to the right.

The high aluminum loadings required for effective catalysis in such systems result in the presence of significant levels of aluminum-containing residues ("ash") in the polymer. This can impair the clarity of finished polymers formed from such catalyst systems.

A further disadvantage of MAO is its limited solubility in paraffinic hydrocarbon solvents. Polymer manufacturers would find it of considerable advantage to have in hand aluminoxane and metallocene-based materials having high paraffin solubility.

Still another disadvantage of MAO has been its relatively high cost. For example, in an article entitled "Economics is Key to Adoption of Metallocene Catalysts" in the Sep. 11, 1995 issue of Chemical & Engineering News, Brockmeier of Argonne National Laboratory concluded that "a reduction in costs or amount of MAO has the potential for greatly reducing the costs to employ metallocene catalysts".

Thus it would be of inestimable value to the art if a way could be found of providing catalyst components based on use of aluminoxanes that are effective co-catalysts for use with transition metal compounds at much lower aluminum-:metal ratios than have been effective heretofore. In addition, the art would be greatly advanced if this could be accomplished with aluminoxane compositions that are less expensive than MAO, that have high solubility in paraffinic solvents and that produce lower ash residues in the polymers.

This invention is deemed to have fulfilled most, if not all, of the foregoing desirable objectives.

BRIEF SUMMARY OF THE INVENTION

This invention makes it possible to provide catalyst compositions in which a low cost co-catalyst can be employed at very low Al loadings. Such catalyst compositions typically have high solubility in paraffinic solvents. Moreover they yield reduced levels of ash and result in improved clarity in polymers formed from such catalyst compositions.

Making all of this possible is the provision pursuant to this invention of a compound which comprises (i) a cation derived from a transition, lanthanide or actinide metal compound, preferably a metallocene, by loss of a leaving group, and (ii) an aluminoxate anion derived by transfer of a proton from a stable or metastable hydroxyaluminoxane to said leaving group. In contrast to aluminoxanes used heretofore and acting as Lewis acids (Eq. 1), the present compositions utilize hydroxyaluminoxane species (HO-AO) acting as Brønsted acids. In the formation of such compounds, a cation is derived from the transition, lanthanide or actinide metal compound by loss of a leaving group, and this cation forms an ion pair with an aluminoxate anion devoid of such leaving group. The leaving group is typically transformed into a neutral hydrocarbon thus rendering the catalyst-forming reaction irreversible as shown in Equation 2:

$$Cp_2MXR+HO\text{-}AO \rightarrow ([Cp_2M\text{-}X]^\oplus(O\text{-}AO)^\ominus + RH \qquad (Eq. 2)$$

Note the absence of the leaving group, X, in the anion $OAO^\ominus$ as compared to the presence of X in the anion, $(X\text{-}MAO)^\ominus$, of Equation 1.

In many of the patents related to the use of aluminoxanes as metallocene co-catalysts, rather broad and generalized assertions have been routinely made regarding aluminum-to-metallocene ratio, types of alkyl aluminoxanes, and ratio of water to aluminum for forming aluminoxanes. However, there is no disclosure of any type that would suggest, let alone demonstrate, the use of an aluminoxane as a Brønsted acid to activate metallocenes and related organometallic catalysts. There are, furthermore, no known prior teachings or descriptions of how to use an alumiinoxane as a Brønsted acid muchless that by so doing it would be possible to reduce the ratio of aluminum to transition, lanthanide or actinide metal to an unprecedentedly low level.

In another of its embodiments this invention provides a process which comprises contacting a transition, lanthanide or actinide metal compound having at least two leaving groups with a hydroxyaluminoxane in which at least one aluminum atom has a hydroxyl group bonded thereto so that one of said leaving groups is lost. As noted above, during the formation of such compounds, an aluminoxate anion is formed that is devoid of the leaving group. Instead the leaving group is typically transformed into a neutral hydrocarbon so that the catalyst forming reaction is irreversible.

Still another embodiment of this invention is a process of polymerizing at least one polymerizable unsaturated monomer, which process comprises contacting said monomer under polymerization conditions with a compound which comprises a cation derived from a transition, lanthanide or actinide metal compound, preferably a metallocene, by loss of a leaving group and an aluminoxate anion derived by transfer of a proton from a stable or metastable hydroxyaluminoxane to said leaving group.

Other embodiments of this invention include catalyst compositions in which a compound comprising a cation derived from a transition, lanthanide or actinide metal compound, preferably a metallocene, by loss of a leaving group and an aluminoxate anion derived by transfer of a proton from a stable or metastable hydroxyaluminoxane to said leaving group is supported on a carrier.

The above and other embodiments, features, and advantages of this invention will become still further apparent from the ensuing description and appended claims.

FURTHER DETAILED DESCRIPTION OF THE INVENTION

Hydroxyaluminoxane Reactants

Figure 1:
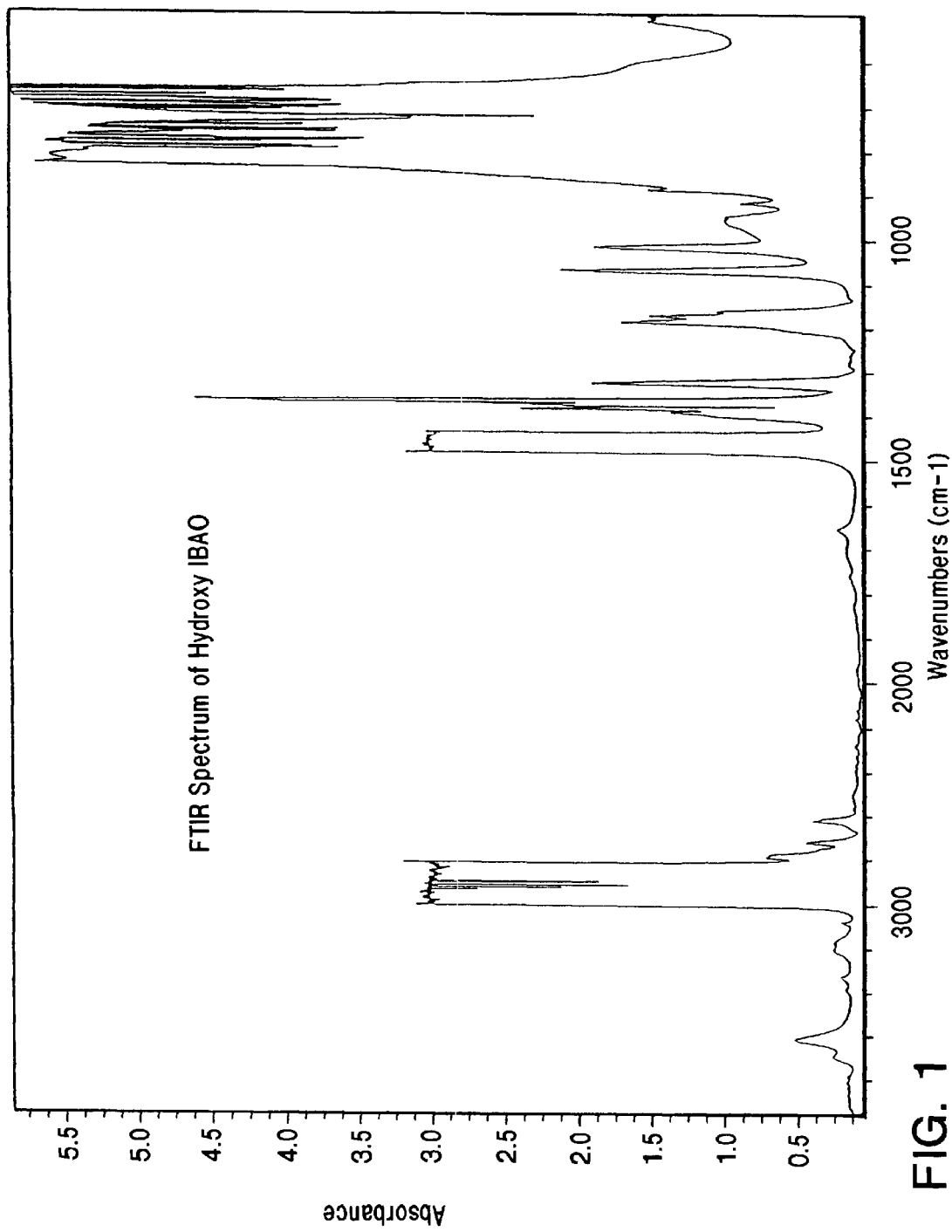
FIG. 1 is an infrared spectrum of hydroxyisobutylaluminoxane (hydroxy IBAO) useful in the practice of this invention.

Unlike catalyst compositions formed from a transition, lanthanide or actinide metal compound (hereinafter "d- or f-block metal compound") and MAO or other previously recognized aluminoxane co-catalyst species, the catalyst compositions of this invention are formed from a hydroxyaluminoxane. The hydroxyaluminoxane has a hydroxyl group bonded to at least one of its aluminum atoms. To form these hydroxyaluminoxanes, a sufficient amount of water is reacted with an alkyl aluminum compound to result in formation of a compound having at least one HO-Al group and having sufficient stability to allow reaction with a d- or f-block organometallic compound to form a hydrocarbon.

The alkyl aluminum compound used in forming the hydroxyaluminoxane reactant can be any suitable alkyl aluminum compound other than trimethylaluminum. Thus at least one alkyl group has two or more carbon atoms. Preferably each alkyl group in the alkyl aluminum compound has at least two carbon atoms. More preferably each alkyl group has in the range of 2 to about 24, and still more preferably in the range of 2 to about 16 carbon atoms. Particularly preferred are alkyl groups that have in the range of 2 to about 9 carbon atoms each. The alkyl groups can be cyclic (e.g., cycloalkyl, alkyl-substituted cycloalkyl, or cycloalkyl-substituted alkyl groups) or acyclic, linear or branched chain alkyl groups. Preferably the alkyl aluminum compound contains at least one, desirably at least two, and most preferably three branched chained alkyl groups in the molecule. Most preferably each alkyl group of the aluminum alkyl is a primary alkyl group, i.e., the alpha-carbon atom of each alkyl group carries two hydrogen atoms.

Suitable aluminum alkyl compounds which may be used to form the hydroxyaluminoxane reactant include dialkylaluminum hydrides and aluminum trialkyls. Examples of the dialkylaluminum hydrides include diethylaluminum hydride, dipropylaluminum hydride, diisobutylaluminum hydride, di(2,4,4-trimethylpentyl)aluminum hydride, di(2-ethylhexyl)aluminum hydride, di(2-butyloctyl)aluminum hydride, di(2,4,4,6,6-pentamethylheptyl)aluminum hydride, di(2-hexyldecyl)aluminum hydride, dicyclopropylcarbinylaluminum hydride, dicyclohexylaluminum hydride, dicyclopentylcarbinylaluminum hydride, and analogous dialkylaluminum hydrides. Examples of trialkylaluminum compounds which may be used to form the hydroxyaluminoxane include triethylaluminum, tripropylaluminum, tributylaluminum, tripentylaluminum, trihexylaluminum, triheptylaluminum, trioctylaluminum, and their higher straight chain homologs; triisobutylaluminum, tris(2,4,4-trimethylpentyl)aluminum, tri-2-ethylhexylaluminum, tris(2,4,4,6,6-pentamethylheptyl)aluminum, tris(2-butyloctyl)aluminum, tris(2-hexyldecyl)aluminum, tris(2-heptylundecyl)aluminum, and their higher branched chain homologs; tri(cyclohexylcarbinyl)aluminum, tri(2-cyclohexylethyl)aluminum and analogous cycloaliphatic aluminum trialkyls. Triisobutylaluminum has proven to be an especially desirable alkyl aluminum compound for producing a hydroxyaluminoxane.

To prepare the hydroxyaluminoxane a solution of the alkyl aluminum compound in an inert solvent, preferably a saturated or aromatic hydrocarbon, is treated with controlled amounts of water while maintaining the vigorously agitated reaction mixture at low temperature, e.g., below about 0° C. When the exothermic reaction subsides, the reaction mixture is stored at a low temperature, e.g., below about 0° C. until used in forming a compound of this invention. When preparing a hydroxyaluminoxane from a low molecular weight alkylaluminum compound, the reaction mixture can be subjected, if desired, to stripping under vacuum at a temperature below room temperature to remove some lower alkane hydrocarbon co-product formed during the reaction. However, such purification is usually unnecessary as the lower alkane co-product is merely an innocuous impurity.

Among suitable procedures for preparing hydroxyaluminoxanes for use in practice of this invention, is the method described by Ikonitskii et al., *Zhurnal Prikladnoi Khimii*, 1989, 62(2), 394–397; and the English language translation thereof available from Plenum Publishing Corporation, copyright 1989, as Document No. 0021-888X/89/6202-0354.

Figure 2:
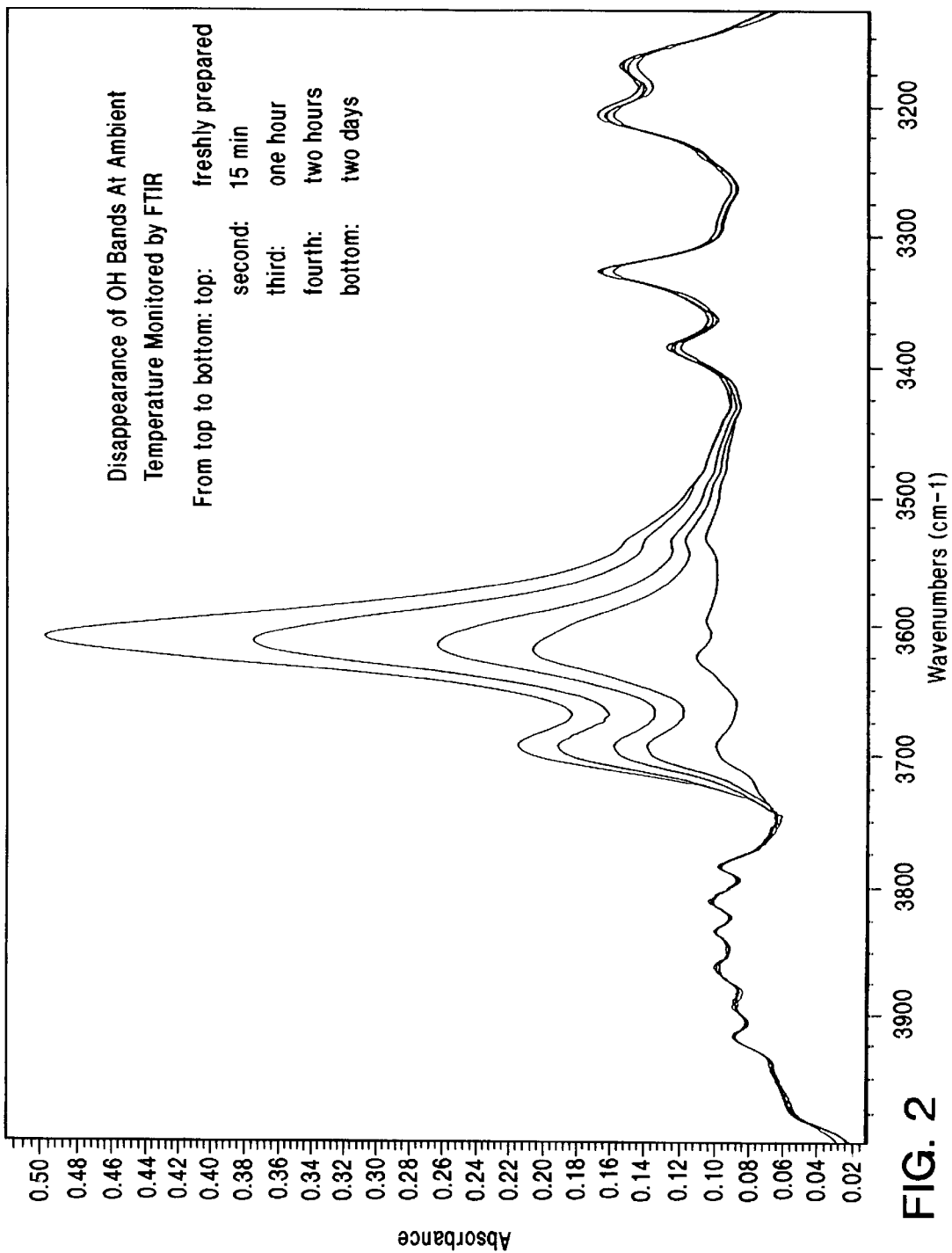
FIG. 2 is a superimposed series of infrared spectra of hydroxy IBAO illustrating the loss of hydroxyl groups at intervals during a two-day period at ambient temperature.
Figure 3:
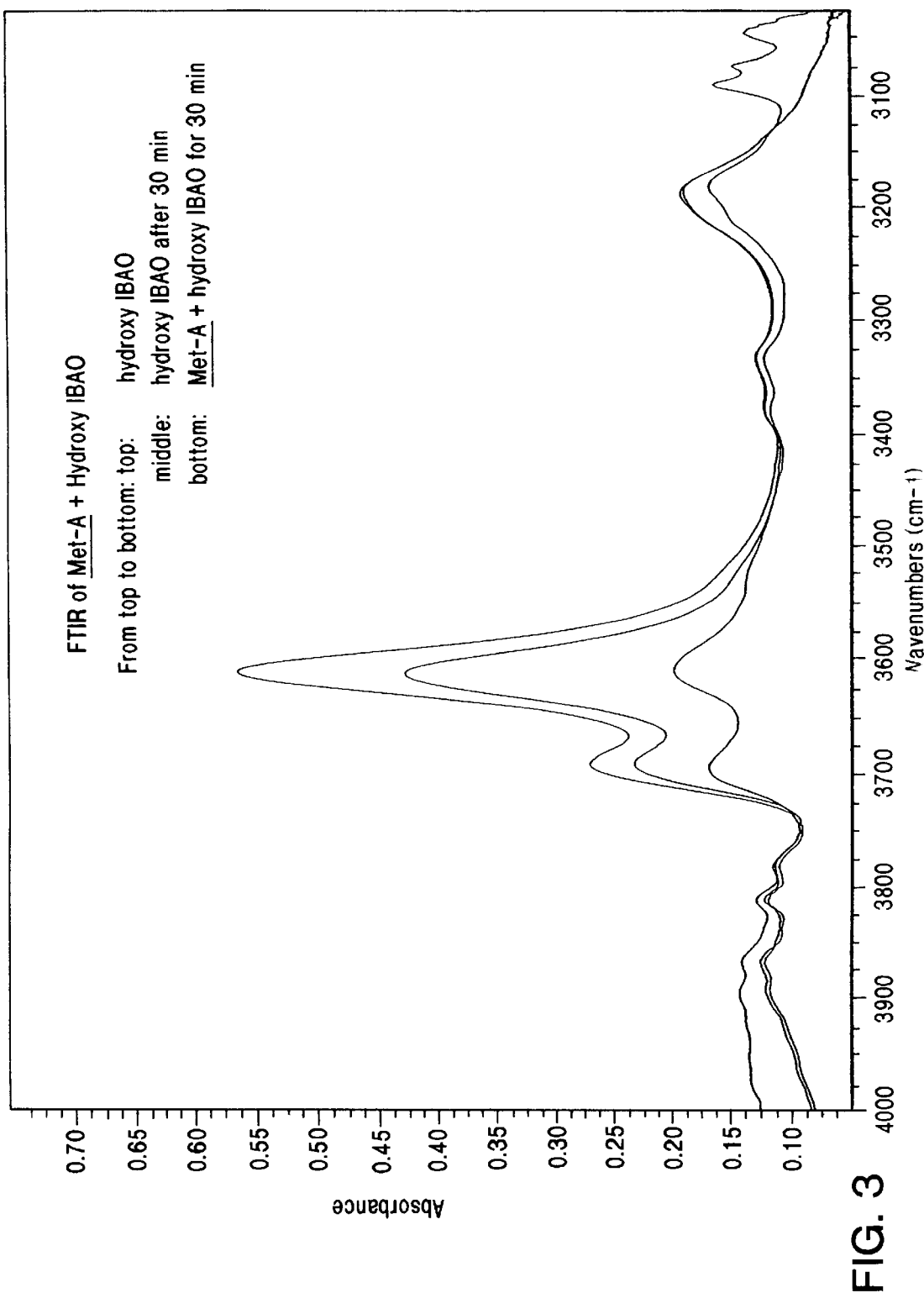
FIG. 3 is a superimposed series of infrared spectra, the top spectrum being that of a fresh hydroxy IBAO, the middle spectrum being that of the same hydroxy IBAO but taken 30 minutes later, and the bottom spectrum being that a catalyst composition of this invention formed from the reaction between rac-dimethylsilylbis(2methylindenyl)zirconium dimethyl (Met-A) and hydroxy IBAO showing that the activation of a metallocene having a suitable leaving group is accompanied by a rapid loss of hydroxyl groups, consistent with HO-IBAO functioning as a Brønsted acid in metallocene activation.

It is very important to maintain the temperature of the hydroxyaluminoxane product solution low enough to slow down the premature loss of its hydroxyl group content sufficiently to maintain a suitable level of OH groups until the activation reaction has been effected. This is demonstrated by the data presented graphically in FIG. 2 which shows the loss of hydroxyl groups from hydroxyisobutylaluminoxane at ambient room temperature in an IR cell. If, on the other hand, the same hydroxyaluminoxane solution is stored in a freezer at −10° C., the rate of hydroxyl group loss is reduced to such a degree that the time scale for preserving the same amount of hydroxyl groups can be lengthened from one to two hours at ambient room temperature to one to two weeks at −10° C. If the hydroxyl group content is lost, the compound reverts to an aluminoxane which is incapable of forming the novel ionic highly active catalytic compounds of this invention.

It is also important when preparing the hydroxyaluminoxanes to use enough water to produce the hydroxyaluminoxane, yet not so much water as will cause its destruction. Typically the water/aluminum mole ratio is in the range of about 0.5/1 to about 1.2/1, and preferably in the range of 0.8/1 to 1.1/1. At least in the case of hydroxyisobutylaluminoxane, these ratios typically result in the formation of hydroxyaluminoxane having at least about one hydroxyl group for every seven aluminum atoms in the overall product. The hydroxyisobutylaluminoxane is essentially devoid of unreacted triisobutylaluminum.

d- or f-Block Metal Compound

Various d- and f-block metal compounds may be used in forming the catalytically active compounds of this invention. The d-block and f-block metals of this reactant are the transition, lanthanide and actinide metals. See, for example, the Periodic Table appearing on page 225 of Moeller, et al., *Chemistry*, Second Edition, Academic Press, Copyright 1984. As regards the metal constituent, preferred are compounds of Fe, Co, Pd, and V. More preferred are compounds of the metals of Groups 4–6 (Ti, Zr, Hf, V, Nb, Ta, Cr, Mo, and W), and most preferred are the Group 4 metals, especially hafnium, and most especially zirconium.

A vital feature of the d- or f-block metal compound used in forming the ionic compounds of this invention is that it must contain at least one leaving group that forms a separate co-product by interaction with a proton from the hydroxyaluminoxane or that interacts with a proton from the hydroxyaluminoxane so as to be converted from a cyclic divalent group into an open chain univalent group bonded to the metal atom of the metallocene. Thus the activity of the chemical bond between the d- or f-block metal atom and the leaving group must be at least comparable to and preferably greater than the activity of the aluminum-carbon bond of the hydroxyaluminoxane. In addition, the basicity of the leaving group must be such that the acidity of its conjugate acid is comparable to or less than the acidity of the hydroxyaluminoxane. Univalent leaving groups that meet these criteria include hydride, hydrocarbyl and silanylcarbinyl ($R_3SiCH_2$—) groups, such as methyl, ethyl, vinyl, allyl, cyclohexyl, phenyl, benzyl, trimethylsilanylcarbinyl, amido, alkylamido, substituted alkylamido, etc. Of these, the methyl group is the most preferred leaving group. Suitable divalent cyclic groups that can serve as leaving groups by a ring opening mechanism whereby a cyclic group is converted into an open chain group that is still bonded to the metal atom of the metallocene include conjugated diene divalent anionic ligand groups such as a conjugated diene or a hydrocarbyl-, halocarbyl-, or silyl substituted derivative thereof, such conjugated diene anionic ligand groups having from 4 to about 40 nonhydrogen atoms and being coordinated to the metal atom of the metallocene so as to form a metallocyclopentene therewith. Typical conjugated diene ligands of this type are set forth for example in U.S. Pat. No. 5,539,068.

Metallocenes make up a preferred class of d- and f-block metal compounds used in making the ionic compounds of this invention. These compounds are characterized by containing at least one cyclopentadienyl moiety pi-bonded to the metal atom. For use in this invention, the metallocene must also have bonded to the d- or f-block metal atom at least one leaving group capable of forming a stable co-product on interaction with a proton from the hydroxyaluminoxane. A halogen atom (e.g., a chlorine atom) bonded to such metal atom is incapable of serving as a leaving group in this regard in as much as the basicities of such halogen atoms are too low.

Such leaving groups may be prepared separately or in situ. For example, metallocene halides may be treated with alkylating agents such as dialkylaluminum alkoxides to generate the desired alkyhnetallocene in situ. Reactions of this type are described for example in WO 95/10546.

Metallocene structures in this specification are to be interpreted broadly, and include structures containing 1, 2, 3 or 4 Cp or substituted Cp rings. Thus metallocenes suitable for use in this invention can be represented by the Formula I:

$$B_a Cp_b ML_c X_d \qquad (I)$$

where Cp independently in each occurrence is a cyclopentadienyl-moiety-containing group which typically has in the range of 5 to about 24 carbon atoms; B is a bridging group or ansa group that links two Cp groups together or alternatively carries an alternate coordinating group such as alkylaminosilylalkyl, silylamido, alkoxy, siloxy, aminosilylalkyl, or analogous monodentate hetero atom electron donating groups; M is a d- or f-block metal atom; each L is, independently, a leaving group that is bonded to the d- or f-block metal atom and is capable of forming a stable co-product on interaction with a proton from a hydroxyaluminoxane; X is a group other than a leaving group that is bonded to the d- or f-block metal atom; a is 0 or 1; b is a whole integer from 1 to 3 (preferably 2); c is at least 2; d is 0 or 1. The sum of b, c, and d is sufficient to form a stable compound, and often is the coordination number of the d- or f-block metal atom.

Cp is, independently, a cyclopentadienyl, indenyl, fluorenyl or related group that can π-bond to the metal, or a hydrocarbyl-, halo-, halohydrocarbyl-, hydrocarbylmetalloid-, and/or halohydrocarbylmetalloid-substituted derivative thereof. Cp typically contains up to 75 non-hydrogen atoms. B, if present, is typically a silylene (—SiR$_2$—), benzo (C$_6$H$_4$<), substituted benzo, methylene (—CH$_2$—), substituted methylene, ethylene (—CH$_2$CH$_2$—), or substituted ethylene bridge. M is preferably a metal atom of Groups 4–6, and most preferably is a Group 4 metal atom, especially hafnium, and most especially zirconium. L can be a divalent substituent such as an alkylidene group, a cyclometallated hydrocarbyl group, or any other divalent chelating ligand, two loci of which are singly bonded to M to form a cyclic moiety which includes M as a member. In most cases L is methyl. X, if present, can be a leaving group or a nonleaving group, and thus can be a halogen atom, a hydrocarbyl group (alkyl, cycloalkyl, alkenyl, cycloalkenyl, aryl, aralkyl, etc.), hydrocarbyloxy, (alkoxy, aryloxy, etc.) siloxy, amino- or substituted amino, hydride, acyloxy, triflate, and similar univalent groups that form stable metallocenes. The sum of b, c, and d is a whole number, and is often from 3–5. When M is a Group 4 metal or an actinide metal, and b is 2, the sum of c and d is 2, c being at least 1. When M is a Group 3 or Lanthanide metal, and b is 2, c is 1 and d is zero. When M is a Group 5 metal, and b is 2, the sum of c and d is 3, c being at least 2.

Also incorporated in this invention are compounds analogous to those of Formula I where one or more of the Cp groups are replaced by cyclic unsaturated charged groups isoelectronic with Cp, such as borabenzene or substituted borabenzene, azaborole or substituted azaborole, and various other isoelectronic Cp analogs. See for example Krishnamurti, et al., U.S. Pat. No. 5,554,775 and 5,756,611.

In one preferred group of metallocenes, b is 2, i.e., there are two cyclopentadienyl-moiety containing groups in the molecule, and these two groups can be the same or they can be different from each other.

Another sub-group of useful metallocenes which can be used in the practice of this invention are metallocenes of the type described in WO 98/32776 published Jul. 30, 1998. These metallocenes are characterized in that one or more cyclopentadienyl groups in the metallocene are substituted by one or more polyatomic groups attached via a N, O, S, or P atom or by a carbon-to-carbon double bond. Examples of such substituents on the cyclopentadienyl ring include —OR, —SR, —NR2, —CH=, —CR=, and —PR$_2$, where R can be the same or different and is a substituted or unsubstituted C$_1$–C$_{16}$ hydrocarbyl group, a tri-C$_1$–C$_8$ hydrocarbylsilyl group, a tri-C$_1$–C$_8$ hydrocarbyloxysilyl group, a mixed C$_1$–C$_8$ hydrocarbyl and C$_1$–C$_8$ hydrocarbyloxysilyl group, a tri-C$_1$–C$_8$ hydrocarbylgermyl group, a tri-C$_1$–C$_8$ hydrocarbyloxygermyl group, or a mixed C$_1$–C$_8$ hydrocarbyl and C$_1$–C$_8$ hydrocarbyloxygermyl group.

Examples of metallocenes to which this invention is applicable include such compounds as:

bis(methylcyclopentadienyl)titanium dimethyl;
bis(methylcyclopentadienyl)zirconium dimethyl;
bis(n-butylcyclopentadienyl)zirconium dimethyl;
bis(dimethylcyclopentadienyl)zirconium dimethyl;
bis(diethylcyclopentadienyl)zirconium dimethyl;
bis(methyl-n-butylcyclopentadienyl)zirconium dimethyl;
bis(n-propylcyclopentadienyl)zirconium dimethyl;
bis(2-propylcyclopentadienyl)zirconium dimethyl;
bis(methylethylcyclopentadienyl)zirconium dimethyl;
bis(indenyl)zirconium dimethyl;
bis(methylindenyl)zirconium dimethyl;
dimethylsilylenebis(indenyl)zirconium dimethyl;
dimethylsilylenebis(2-methylindenyl)zirconium dimethyl;
dimethylsilylenebis(2-ethylindenyl)zirconium dimethyl;
dimethylsilylenebis(2-methyl-4-phenylindenyl)zirconium dimethyl;
1,2-ethylenebis(indenyl)zirconium dimethyl;
1,2-ethylenebis(methylindenyl)zirconium dimethyl;
2,2-propylidenebis(cyclopentadienyl)(fluorenyl)zirconium dimethyl;
dimethylsilylenebis(6-phenylindenyl)zirconium dimethyl;
bis(methylindenyl)zirconium benzyl methyl;
ethylenebis[2-(tert-butyldimethylsiloxy)-1-indenyl]zirconium dimethyl;
dimethylsilylenebis(indenyl)chlorozirconium methyl;
5-(cyclopentadienyl)-5-(9-fluorenyl)1-hexene zirconium dimethyl;
dimethylsilylenebis(2-methylindenyl)hafnium dimethyl;
dimethylsilylenebis(2-ethylindenyl)hafnium dimethyl;
dimethylsilylenebis(2-methyl4-phenylindenyl)hafnium dimethyl;
2,2-propylidenebis(cyclopentadienyl)(fluorenyl)hafnium dimethyl;
bis(9-fluorenyl)(methyl)(vinyl)silane zirconium dimethyl, bis(9-fluorenyl)(methyl)(prop-2-enyl)silane zirconium dimethyl,
bis(9-fluorenyl)(methyl)(but-3-enyl)silane zirconium dimethyl,
bis(9-fluorenyl)(methyl)(hex-5-enyl)silane zirconium dimethyl,
bis(9-fluorenyl)(methyl)(oct-7-enyl)silane zirconium dimethyl,
(cyclopentadienyl)(1-allylindenyl)zirconium dimethyl,
bis(1-allylindenyl)zirconium dimethyl,
(9-(prop-2-enyl)fluorenyl)(cyclopentadienyl)zirconium dimethyl,
(9-(prop-2-enyl)fluorenyl)(pentamethylcyclopentadienyl)zirconium dimethyl,
bis(9-(prop-2-enyl)fluorenyl)zirconium dimethyl,
(9-(cyclopent-2-enyl)fluorenyl)(cyclopentadienyl)zirconium dimethyl,
bis(9-(cyclopent-2-enyl)(fluorenyl)zirconium dimethyl,
5-(2-methylcyclopentadienyl)-5-(9-fluorenyl)-1-hexene zirconium dimethyl,
1-(9-fluorenyl)-1-(cyclopentadienyl)-1-(but-3-enyl)-1-(methyl)methane zirconium dimethyl,
5-(fluorenyl)-5-(cyclopentadienyl)-1-hexene hafnium dimethyl,
(9-fluorenyl)(1-allylindenyl)dimethylsilane zirconium dimethyl,
1-(2,7-di(alpha-methylvinyl)(9-fluorenyl)-1-(cyclopentadienyl)-1,1-dimethylmethane zirconium dimethyl,
1-(2,7-di(cyclohex-1-enyl)(9-fluorenyl))-1-(cyclopentadienyl)-1,1-methane zirconium dimethyl,
5-(cyclopentadienyl)-5-(9-fluorenyl)-1-hexene titanium dimethyl,
5-(cyclopentadienyl)-5-(9-fluorenyl)1-hexene titanium dimethyl,
bis(9-fluorenyl)(methyl)(vinyl)silane titanium dimethyl,
bis(9-fluorenyl)(methyl)(prop-2-enyl)silane titanium dimethyl,
bis(9-fluorenyl)(methyl)(but-3-enyl)silane titanium dimethyl,
bis(9-fluorenyl)(methyl)(hex-5-enyl)silane titanium dimethyl,
bis(9-fluorenyl)(methyl)(oct-7-enyl)silane titanium dimethyl,
(cyclopentadienyl)(1-allylindenyl)titanium dimethyl,
bis(1-allylindenyl)titanium dimethyl,
(9-(prop-2-enyl)fluorenyl)(cyclopentadienyl)hafnium dimethyl,
(9-(prop-2-enyl)fluorenyl)(pentamethylcyclopentadienyl) hafnium dimethyl,
bis(9-(prop-2-enyl)fluorenyl)hafnium dimethyl,
(9-(cyclopent-2-enyl)fluorenyl)(cyclopentadienyl) hafnium dimethyl,
bis(9-(cyclopent-2-enyl)(fluorenyl)hafnium dimethyl,
5-(2-methylcyclopentadienyl)-5-(9-fluorenyl)-1-hexene hafnium dimethyl,
5-(fluorenyl)-5-(cyclopentadienyl)-1-octene hafnium dimethyl,
(9-fluorenyl)(1-allylindenyl)dimethylsilane hafnium dimethyl.
(tert-butylamido)dimethyl(tetramethylcyclopentadienyl)silane titanium(1,3-pentadiene);
(cyclopentadienyl)(9-fluorenyl)diphenylmethane zirconium dimethyl;
(cyclopentadienyl)(9-fluorenyl)diphenylmethane hafnium dimethyl;
dimethylsilanylene-bis(indenyl)thorium dinethyl;
dimethylsilanylene-bis(4,7-dimethyl-1-indenyl) zirconium dimethyl;
dimethylsilanylene-bis(indenyl)uranium dimethyl;
dimethylsilanylene-bis(2-methyl-4-ethyl-1-indenyl) zirconium dimethyl;
dimethylsilanylene-bis(2-methyl-4,5,6,7-tetrahydro-1-indenyl)zirconium dimethyl;
(tert-butylamido)dimethyl(tetramethyl-$\eta^5$-cyclopentadienyl)silane titanium dimethyl;
(tert-butylamido)dimethyl(tetramethyl-$\eta^5$-cyclopentadienyl)silane chromium dimethyl;
(tert-butylamido)dimethyl(tetramethyl-$\eta^5$-cyclopentadienyl)silane titanium dimethyl;
(phenylphosphido)dimethyl(tetramethyl-$\eta^5$-cyclopentadienyl)silane titanium dimethyl; and
[dimethylsilanediylbis(indenyl)]scandium methyl.

In many cases the metallocenes such as referred to above will exist as racemic mixtures, but pure enantiomeric forms or mixtures enriched in a given enantiomeric form can be used.

A feature of this invention is that not all metallocenes can produce compositions having the excellent catalytic activity possessed by the compositions of this invention. For example, in the absence of a separate metal alkyl compound, bis(cyclopentadienyl)dichlorides of Zr cannot produce the compositions of this invention because the chloride atoms are not capable of serving as leaving groups under the conditions used in forming the compositions of this invention. Moreover, the fact that two different metallocenes of the same metal have the same suitable leaving groups (e.g., methyl groups) does not, in and of itself, guarantee that they both will form compositions having the excellent catalytic activity possessed by the compositions of this invention. To illustrate, while rac-dimethylsilylbis(2-methyl-1-indenyl) zirconium dimethyl has produced a highly active catalyst composition of this invention, rac-ethylenebis(1-indenyl) zirconium dimethyl has little or no catalytic activity under the identical conditions employed. The reason for this dichotomy is completely unknown. One might speculate that the fit and tightness of the cation-anion ion pairing may be the underlying factor determining catalytic activity, as has been observed in the case of a metallocene activator, triphenyl carbenium tris(2,2',2'-nonafluorobiphenyl) fluoroaluminate, as recently reported by Chen et al., *J. Am. Chem. Soc.*, 1998, 120, 6287, and *J. Am. Chem. Soc.*, 1997, 119, 2582. However, thus far no satisfactory postulate muchless a scientifically valid explanation has been adduced. Thus on the basis of the state of present knowledge, in order to practice this invention, it is desirable to perform preliminary tests with any given previously untested metallocene to determine catalytic activity of the product of reaction with a hydroxyaluminoxane. In conducting such preliminary tests, use of the procedures and reaction conditions of the Examples presented hereinafter, or suitable adaptations thereof, is recommended.

Reaction Conditions

To produce the catalytically active catalyst compositions of this invention the reactants, the d- or f-block metal compound, and the hydroxyaluminoxane that has either been freshly prepared or stored at low temperature (e.g., −10° C. or below) are brought together preferably in solution form or on a support. The reaction between the hydroxy group and the bond between the leaving group and the d- or f-block metal is stoichiometric and thus the proportions used should be approximately equimolar. The temperature of the reaction mixture is kept in the range of about −78 to about 160° C. and preferably in the range of about 15 to about 30° C. The reaction is conducted under an inert atmosphere and in an inert environment such as in an anhydrous solvent medium. Reaction times are short, typically within four hours. When the catalyst composition is to be in supported form on a catalyst support or carrier, the suitably dried, essentially hydrate-free support can be included in the reaction mixture. However, it is possible to add the catalyst to the support after the catalyst composition has been formed.

Polymerization Processes Using Catalysts of this Invention

The catalyst compositions of this invention can be used in solution or deposited on a solid support. When used in solution polymerization, the solvent can be, where applicable, a large excess quantity of the liquid olefinic-monomer. Typically, however, an ancillary inert solvent, typically a liquid paraffinic or aromatic hydrocarbon solvent is used, such as heptane, isooctane, decane, toluene, xylene, ethylbenzene, mesitylene, or mixtures of liquid paraffinic hydrocarbons and/or liquid aromatic hydrocarbons. When the catalyst compositions of this invention are supported on a carrier, the solid support or carrier can be any suitable particulate solid, and particularly a porous support such as talc, zeolites, or inorganic oxides, or resinous support material such as polyolefins. Preferably, the support material is an inorganic oxide in finely divided form.

Suitable inorganic oxide support materials which are desirably employed include metal oxides such as silica, alumina, silica-alumina and mixtures thereof. Other inorganic oxides that may be employed either alone or in combination with the silica, alumina or silica-alumina are magnesia, titania, zirconia, and like metal oxides. Other suitable support materials are finely divided polyolefins such as finely divided polyethylene.

Polymers can be produced pursuant to this invention by homopolymerization of polymerizable olefins, typically 1-olefins (also known as α-olefins) such as ethylene, propylene, 1-butene, styrene, or copolymerization of two or more copolymerizable monomers, at least one of which is typically a 1-olefin. The other monomer(s) used in forming such copolymers can be one or more different 1-olefins and/or a diolefin, and/or a polymerizable acetylenic monomer. Olefins that can be polymerized in the presence of the catalysts of this invention include a-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Normally, the hydrocarbon monomers used, such as 1-olefins, diolefins and/or acetylene monomers, will contain up to about 10 carbon atoms per molecule. Preferred 1-olefin monomers for use in the process include ethylene, propylene, 1-butene, 3-methyl1-butene, 4-methyl-1-pentene, 1-hexene, and 1-octene. It is particularly preferred to use supported or unsupported catalysts of this invention in the polymerization of ethylene, or propylene, or ethylene and at least one $C_3$–$C_8$ 1-olefin copolymerizable with ethylene. Typical diolefin monomers which can be used to form terpolymers with ethylene and propylene include butadiene, hexadiene, norbornadiene, and similar copolymerizable diene hydrocarbons. 1-Heptyne and 1-octyne are illustrative of suitable acetylenic monomers which can be used.

Polymerization of ethylene or copolymerization with ethylene and an α-olefin having 3 to 10 carbon atoms may be performed in either the gas or liquid phase (e.g. in a solvent, such as toluene, or heptane). The polymerization can be conducted at conventional temperatures (e.g., 0° to 120° C.) and pressures (e.g., ambient to 50 kg/cm$^2$) using conventional procedures as to molecular weight regulations and the like.

The heterogeneous catalysts of this invention can be used in polymerizations conducted as slurry processes or as gas phase processes. By "slurry" is meant that the particulate catalyst is used as a slurry or dispersion in a suitable liquid reaction medium which may be composed of one or more ancillary solvents (e.g., liquid aromatic hydrocarbons, etc.) or an excess amount of liquid monomer to be polymerized in bulk. Generally speaking, these polymerizations are conducted at one or more temperatures in the range of about 0 to about 160° C., and under atmospheric, subatmospheric, or superatmospheric conditions. Conventional polymerization adjuvants, such as hydrogen, may be employed if desired. Preferably polymerizations conducted in a liquid reaction medium containing a slurry or dispersion of a catalyst of this invention are conducted at temperatures in the range of about 40 to about 110° C. Typical liquid diluents for such processes include hexane, toluene, and like materials. Typically, when conducting gas phase polymerizations, superatmospheric pressures are used, and the reactions are conducted at temperatures in the range of about 50 to about 160° C. These gas phase polymerizations can be performed in a stirred or fluidized bed of catalyst in a pressure vessel adapted to permit the separation of product particles from unreacted gases. Thermostated ethylene, comonomer, hydrogen and an inert diluent gas such as nitrogen can be introduced or recirculated to maintain the particles at the desired polymerization reaction temperature. An aluminum alkyl such as triethylaluminum may be added as a scavenger of water, oxygen and other impurities. In such cases the aluminum alkyl is preferably employed as a solution in a suitable dry liquid hydrocarbon solvent such as toluene or xylene. Concentrations of such solutions in the range of about $5\times10^{-5}$ molar are conveniently used. But solutions of greater or lesser concentrations can be used, if desired. Polymer product can be withdrawn continuously or semi-continuously at a rate that maintains a constant product inventory in the reactor.

The catalyst compositions of this invention can also be used along with small amounts of hydrocarbylborane compounds such as triethylborane, tripropylborane, tributylborane, tri-sec-butylborane. When so used, molar Al/B ratios in the range of about 1/1 to about 1/500 can be used.

Because of the high activity and productivity of the catalysts of this invention, the catalyst levels used in olefin polymerizations can be less than previously used in typical olefin polymerizations conducted on an equivalent scale. In general, the polymerizations and copolymerizations conducted pursuant to this invention are carried out using a catalytically effective amount of a novel catalyst composition of this invention, which amount may be varied depending upon such factors such as the type of polymerization being conducted, the polymerization conditions being used, and the type of reaction equipment in which the polymerization is being conducted. In many cases, the amount of the catalyst of this invention used will be such as to provide in the range of about 0.000001 to about 0.01 percent by weight of d- or f-block metal based on the weight of the monomer(s) being polymerized.

After polymerization and deactivation of the catalyst in a conventional manner, the product polymer can be recovered from the polymerization reactor by any suitable means. When conducting the process with a slurry or dispersion of the catalyst in a liquid medium the product typically is recovered by a physical separation technique (e.g. decantation, etc.). The recovered polymer is usually washed with one or more suitably volatile solvents to remove residual polymerization solvent or other impurities, and then dried, typically under reduced pressure with or without addition of heat. When conducting the process as a gas phase polymerization, the product after removal from the gas phase reactor is typically freed of residual monomer by means of a nitrogen purge, and often can be used without further catalyst deactivation or catalyst removal.

When preparing polymers pursuant to this invention conditions may be used for preparing unimodal or multimodal polymer types. For example, mixtures of catalysts of this invention formed from two or more different metallocenes having different propagation and termination rate constants for ethylene polymerizations can be used in preparing polymers having broad molecular weight distributions of the multimodal type.

The following Examples are presented for purposes of illustration and not limitation. All operations of these Examples were carried out under nitrogen either in a drybox with below 1 ppm oxygen or using standard Schlenk line techniques. Aluminum alkyl compounds, methylaluminoxane (MAO) and triisobutylaluminum (TIBA), were commercial products of Albemarle Corporation and used as received. Reagents benzylmagnesium chloride and MeLi with LiBr were purchased from Aldrich and used as received. Toluene, ethylene, propylene, and nitrogen used in the polymerization reactions were purified by passing through a series of three cylinders: molecular sieves, Oxyclear oxygen absorbent, and alumina. Ethylene and propylene were polymer grade from Matheson. Toluene for catalyst preparation and spectroscopy studies was Aldrich anhydrous grade and was distilled from sodium/benzophenone ketyl. Hexane was Aldrich anhydrous grade and stored over Na/K alloy. The metallocenes used in these Examples were prepared according to procedures given in the literature. Thus $Cp_2ZrMe_2$ was prepared using the method of Samuel, et al., *J. Am. Chem. Soc.*, 1973, 95, 6263; rac-dimethylsilylbis(2-methyl-1-indenyl)zirconium dichloride using the method of Spaleck, et al., *Angew. Chem., Int. Ed. Engl.*, 1992, 31, 1347, and Winter, et al. U.S. Pat. No. 5,145,819; and bis(1-methyl-3-n-butyl-cyclopentadienyl)zirconium dichloride using the method of Lee, et al., Canadian Pat. No. 2,164,914, July 1996. The FT-infrared spectra were recorded on a Nicolet Magna-IR 750 spectrometer with 32 scans and 2 $cm^{-1}$ resolution using 0.5 mm NaCl cells. The absorption of hexane was compensated by subtraction with a reference hexane spectrum acquired from the same cell. The Uv-Vis spectra were recorded in the 290–700 nm region on a Varian Cary 3E spectrometer. Quartz cuvettes of 1 cm pathlength were used.

EXAMPLE 1

Rac-dimethylsilylbis(2-methylindenyl)zirconium dimethyl (MET-A)

Rac-dimethylsilylbis(2-methylindenyl)zirconium dichloride (5.03 g, 10.55 mmol) was suspended in 100 g of toluene. The orange slurry was heated in an oil bath to 40° C. Most of the orange-yellow metallocene remained undissolved. MeLi/LiBr (5.87 wt % in ether, 7.78 g) was added dropwise over two hours. The solution became amber/yellow and the solids lightened. The reaction was allowed to cool to ambient temperature and stir overnight. Analysis of the reaction showed 9.3 mol % of mono-methyl intermediates. Additional aliquots of MeLi/LiBr (1.66 g) were added dropwise until the monomethyl intermediates were reduced to less than two mol %. Approximately a quarter of the solvent was removed in vacuo and then the lithium salts were filtered on a medium frit and washed with 20 mL of toluene. The combined filtrates were concentrated in vacuo. A yellow crystalline solid formed. The slurry was cooled to −20° C. The yellow crystals were filtered on a coarse frit. After drying in vacuo, the yield of rac-dimethylsilylbis(2-methylindenyl)zirconium dimethyl was 3.20 g (70%).

EXAMPLE 2

Bis(1-butyl-3-methylcyclopentadienyl)zirconium dimethyl (MET-B)

Bis(1-butyl-3-methylcyclopentadienyl)zirconium dichloride (2.71 g, 6.26 mmol) was dissolved in 21.4 g of toluene. Low-halide MeLi (~1.5 M in ether, 8.0 mL) was added dropwise at ambient temperature. A white solid formed immediately. The reaction was allowed to stir for 1.5 hours. Analysis of the reaction showed 3.5 mol % of mono-methyl intermediate. An additional aliquot of MeLi (0.4 mL) was then added to consume the monomethyl intermediate. After stirring overnight, the supernatant liquid was reanalyzed to verify that the reaction was complete. The slurry was filtered on a medium frit and the solvent was removed in vacuo. A light yellow liquid of bis(1-butyl-3-methylcyclopentadienyl)zirconium dimethyl remained (2.13 g, 87% yield).

EXAMPLE 3

Synthesis of Hydroxyisobutylaluminoxane (HO-IBAO)

The reaction was carried out in a 1-L, three-necked, round-bottomed Morton flask equipped with a thermometer, an outlet connected to a Schlenk line, and a rubber septum through which water was added via a syringe needle. To this flask containing a solution of triisobutylaluminum (98.4 g, 492.4 mmol) in hexane (276.4 g) with vigorous magnetic stirring was added degassed water (8.85 g, 491.4 mmol) using a syringe pump over a period of 65 minutes. The temperature was maintained at between −5 and 0° C. by applying a dry ice bath (without acetone) and by adjusting water addition speed. After the water addition was complete, the solution was stirred for an additional ten minutes (or until the exothermic reaction subsided, which usually lasts about 5–10 minutes after completion of water addition), stripped of dissolved isobutane and some hexane under vacuum at a temperature somewhat below ambient, transferred, and stored in a −10° C. freezer in a drybox. The solution weighed 252.2 g and was determined by analysis to have a wt % Al of 5.15.

EXAMPLE 4

Synthesis of Deuteroxyisobutylaluminoxane (DO-IBAO)

The procedure of Example 3 was repeated with the exception that an equivalent amount of $D_2O$ was used in place of the water and the operation was conducted with similar amounts of the reactants.

EXAMPLE 5

Characterization of HO-IBAO by TR-Spectroscopy

The presence of hydroxyl groups in the product solution of Example 3 was indicated by an infrared spectrum (see FIG. 1) taken the next day. Initially, there are two types of hydroxyl groups detected at 3615 cm$^{-1}$ (major) and 3695 cm$^{-1}$ (minor), respectively. At room temperature, both are unstable particularly the major one. The stability study was carried out with another reaction solution in hexane (Al wt %=3.55, H$_2$O/Al=1.00). The liquid cuvette was left in the IR chamber at ambient temperature and spectra were recorded at the indicated intervals (see FIG. 2). The last spectrum taken after two days at ambient temperature, revealed possibly two additional OH frequencies at 3597 cm$^{-1}$ and 3533 cm$^{-1}$. The stability of the hydroxyls groups depends on a number of factors. For instance, the hydroxyl groups can be preserved for a much longer time if the solution is kept at a lower temperature, or if added tetrahydrofuran which stabilizes the hydroxyls both by forming hydrogen-bonds, and by coordinating to aluminum sites; or by using a higher hydrolysis ratio (hydroxyls are more stable in IBAO of water/Al=1.00 than in IBAO of water/Al=0.90).

As indicated by Example 4, the hydroxyl groups can be replaced by deuteroxy groups by hydrolyzing TIBA with D$_2$O. A new IR band assignable to OD stretching appeared at 2665 cm$^{-1}$ corresponding to the 3615 cm$^{-1}$ band for OH stretching (the corresponding OD band for the 3695 cm$^{-1}$ stretching is not seen, presumably obscured by large C-H bands nearby). The ratio of two frequencies ($n_{OH}/n_{OD}$= 1.356) indicates that this OH or OD group is free or not engaged in any intra or intermolecular hydrogen bonding (the theoretical value is 1.35 which falls systematically as the strengths of the hydrogen bond increases; see L. J. Bellamy, *The Infrared Spectra of Complex Molecules*, Volume Two, Second Edition, 1980, page 244, Chapman and Hall). Deuterated isobutane, (CH$_3$)$_2$CHCH$_2$D, a by-product of the hydrolysis reaction, was also detected by IR as two equally intense bands at 2179 cm$^{-1}$ and 2171 cm$^{-1}$, respectively.

To enable correlation between IR absorbance and hydroxy content of HO-IBAO, a quantitative determination of hydroxy content was performed (Example 6). In the absence of a model compound with known hydroxy content, IR spectroscopy provides only qualitative information.

EXAMPLE 6

Quantification of Hydroxy Content in HO-IBAO; Benzyl Grignard Method

To a cold, vigorously stirred HO-IBAO solution (5.52 g solution, 10 mmol Al) with a 4.89 wt % Al and an IR absorbance of 0.557 for the 3616 cm$^{-1}$ band was added a 2-M solution of benzylmagnesium chloride in THF (2.0 ml, 4 mmol). The mixture quickly reacted becoming two layers and was stirred at ambient temperature for 90 minutes. After that, the resulting suspension was vacuum distilled at temperatures up to 50° C. over one hour and all volatiles were trapped in a flask cooled by a liquid nitrogen bath. The amount of toluene in the collected liquid was determined by GC (with a known amount of pentadecane added as an internal reference) to be 0.66 mmol, which corresponds to 6.6 OH groups for every 100 Al atoms.

The mechanism as depicted in Equation (2) above was proved by the use of two different experiments, one involving deuterium labeling and GC-mass spectographic analysis (Examples 7 and 8), and the other infra-red analysis (Example 7).

EXAMPLE 7

Verification of Novel Metallocene Activation Mechanism; HO-IBAO Functions As a Brønsted Acid Use of Deuterium-Labeled Reactant (DO-IBAO) with Unbridged Metallocene. Into a 30-mL round-bottomed flask containing a cold solution of deuteroxyisobutylaluminoxane (DO-IBAO) (OD stretching at 2665 cm$^{-1}$, about 5–7 OD for every 100 Al) (3.31 wt % Al, 9.26 g solution, 11.4 mmol Al) prepared by hydrolyzing the TIBA with D$_2$O was added solid bis(cyclopentadienyl)zirconium dimethyl (Cp$_2$ZrMe$_2$) (33 mg, 0.13 mmol). The flask was immediately closed with a gas tight septum to prevent escape of any gaseous products. The volume of the solution was ca. 15 mL which left about another 15 mL of headspace in the flask. It took about 2–3 minutes for the metallocene solids to dissolve completely to give a light yellow solution. After stirring for 85 minutes at ambient temperature, a gaseous sample withdrawn from the head space of the flask was subjected to GC-Mass Spec analysis which showed a composition of 9.1 mol % CH$_3$D and 90.9 mol % N$_2$. In other words, 1.37 mL of the 15-mL headspace was CH$_3$D, which corresponds to 43% of the theoretical amount predicted by the reaction of Equation (2) above. The amount of CH$_3$D remained dissolved in the solution was not determined. (In fact, if the solution was cooled to −10 to −20° C., CH$_3$D in the headspace became too little to be detectable by GC-Mass Spec).

EXAMPLE 8

Verification of Novel Metallocene Activation Mechanism; HO-IBAO Functions As a Brønsted Acid Use of Deuterium-Labeled Reactant (DO-IBAO) with Bridged Metallocene. This reaction was carried out analogously to Example 7 above except that the reactants were rac-dimethylsilylbis(2-methyl-1-indenyl)zirconium dimethyl (45 mg, 0.103 mmol) and DO-IBAO (12.23 g, 15.0 mmol Al) and the flask contained about 19-mL of solution and 11-mL of headspace. The GC-Mass Spec analysis showed a 4.8 mol % of CH$_3$D in the headspace, which corresponds to 21% of the theoretical amount. The lower percentage reflects the fact that the flask had less headspace and more solution volume for CH$_3$D to dissolve in.

EXAMPLE 9

Verification of Novel Metallocene Activation Mechanism; HO-IBAO Functions As a Brønsted Acid Use of Infra-Red Analysis of Product from HO-IBAO and a Metallocene. To a cold, freshly prepared HO-IBAO (3.0 mmol Al, IR spectrum shown in FIG. 4(*a*)) in hexane was added solid dimethylsilylbis(methylindenyl)zirconium dimethyl (0.1 mmol, Al/Zr=30). After stirring at ambient temperature for 30 minutes, the resulting deep red-brown solution was taken a IR spectrum shown in FIG. 4(*c*). Separately, another portion of the same cold HO-IBAO solution was allowed to stand at ambient temperature for 30 minutes and its IR spectrum was taken immediately thereafter (shown in FIG. 4(*b*). It is clear from this set of three spectra that the reaction between HO-IBAO and the metallocene results in a rapid disappearance of the hydroxyl groups in IBAO, which cannot be accounted for by the slower self-consumption during the same period.

EXAMPLE 10

Figure 4:
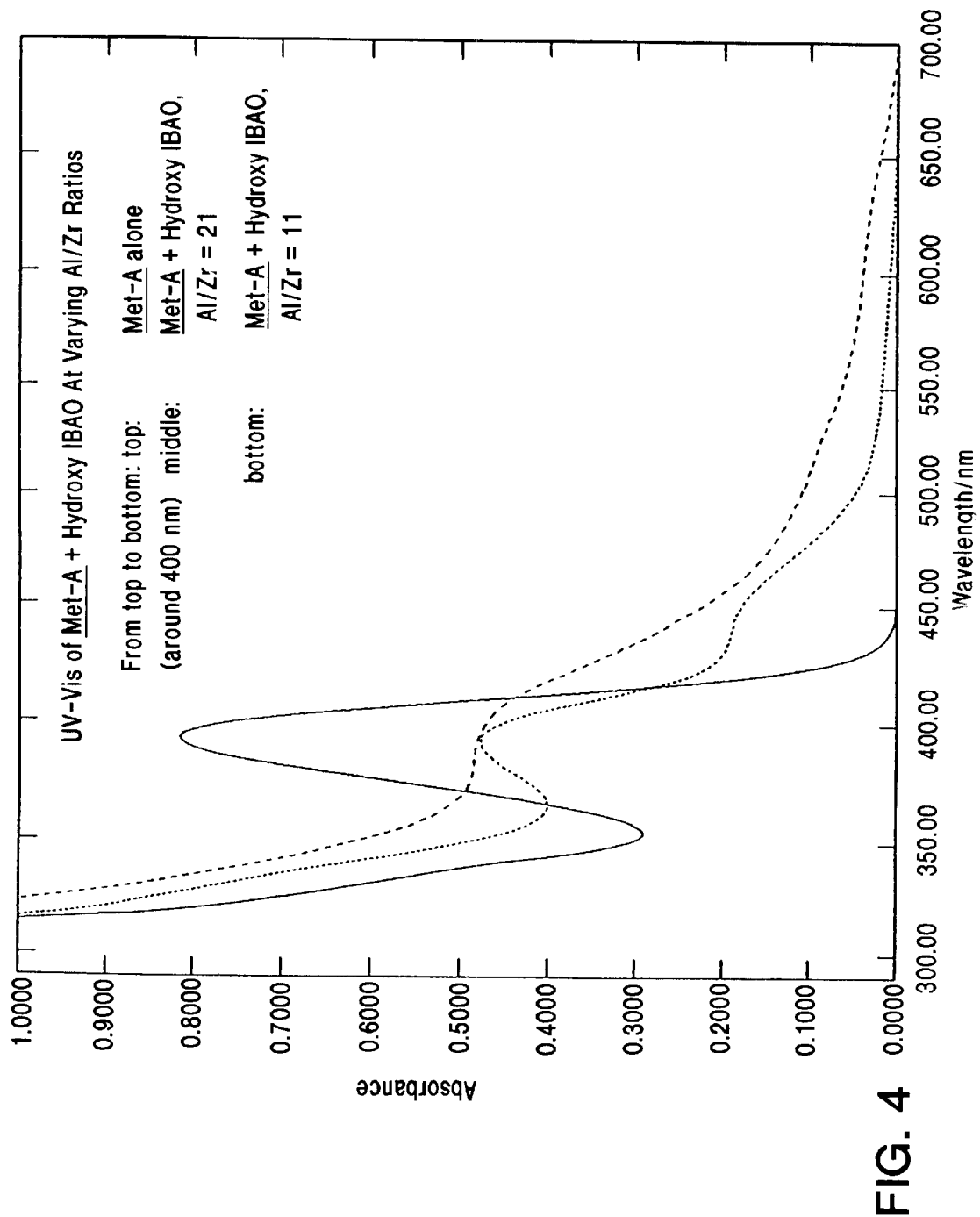
FIG. 4 are superimposed UV-Vis spectra, the top spectrum being that of Met-A, the middle spectrum being that of a catalyst composition of this invention having an Al/Zr ratio of 21/1 formed from the reaction between Met-A and hydroxy IBAO, and the bottom spectrum being that of a catalyst composition of this invention having an Al/Zr ratio of 11/1 formed from the reaction between Met-A and hydroxy IBAO.

UV-Vis Spectra of rac-dimethylsilylbis(2-methylindenyl)zirconium dimethyl+Hydroxy TBAO With Varying Al/Zr Ratios The reaction between hydroxy IBAO and methylated metallocene can be readily monitored by UV-Vis. It has been reported that the ligand-to-metal charge transfer (LMCT) bands undergo a characteristic bathochromic shift (shorter to longer wavelength) upon converting from a neutral metallocene (catalyst precursor) to a metallocenium cation (active catalyst) by an activator (Siedle, et al., *Macromol. Symp.*, 1995, 89, 299; Pieters, et al., *Macromol. Rapid Commun.*, 1995, 16, 463). For rac-dimethylsilylbis(2-methylindenyl)-zirconium dimethyl, an LMCT band (see FIG. 4-solid) appearing at 394 nm ($\lambda_{max}$, 4710 $M^{-1}$ $cm^{-1}$) serves as a convenient probe to measure the progress of the activation reaction. As shown in FIG. 4-dotted, the more hydroxy IBAO is used, the more the starting metallocene is consumed and the more adsorption is observed in the longer wavelength region. It is clear from the spectra that an Al/Zr ratio of 21 is almost enough to activate all of the metallocene.

Figure 5:
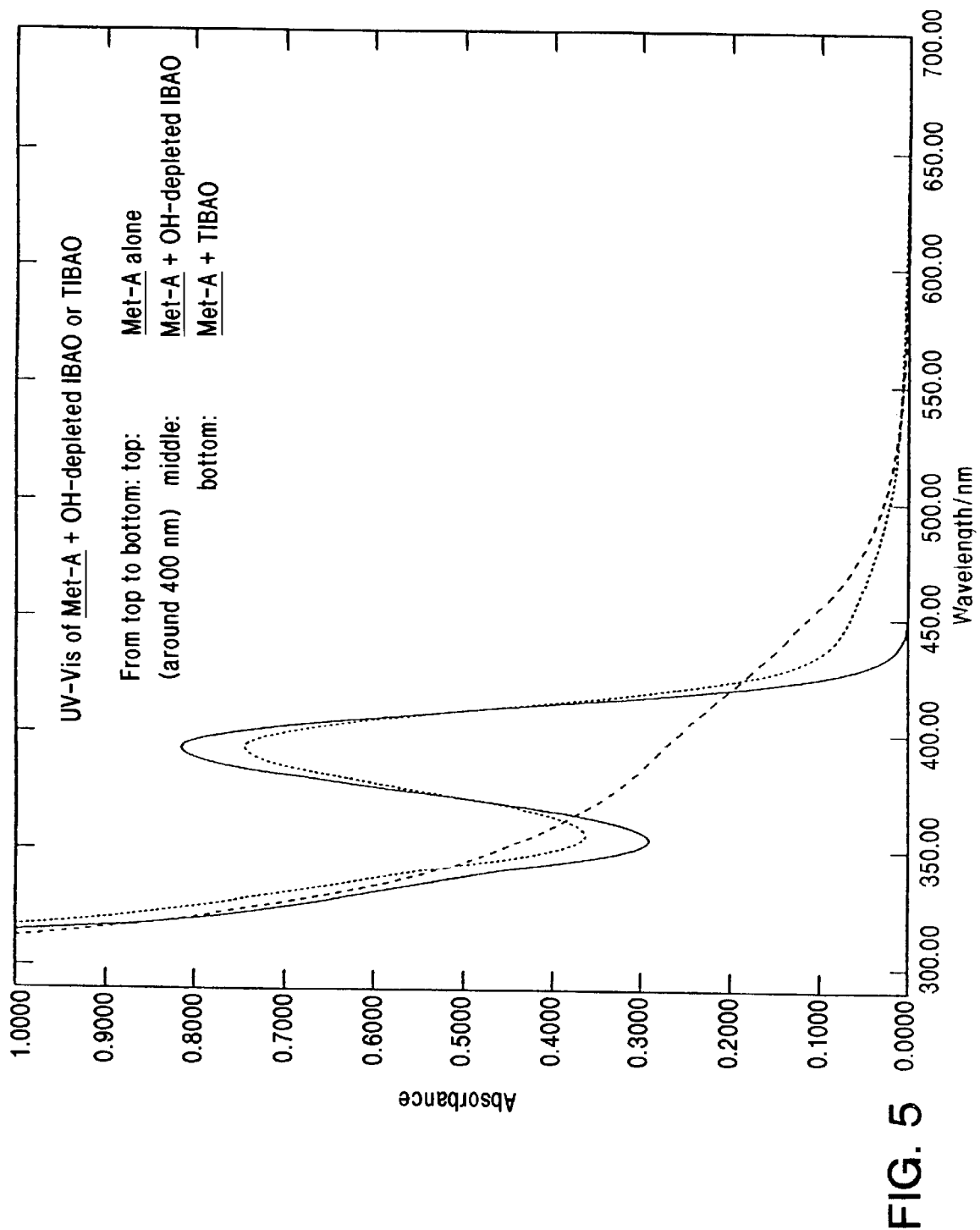
FIG. 5 are superimposed UV-Vis spectra, the top spectrum being that of Met-A, the middle spectrum being that of a composition formed from Met-A and isobutylaluminoxane (IBAO) that resulted from loss or depletion of hydroxyl groups from IBAO, and the bottom spectrum being that of tetraisobutyldialuminoxane (TIBAO).

As reference to FIG. 5 shows, this spectroscopy tool is also useful for measuring the effectiveness of a metallocene activator. Thus, a hydroxy-depleted isobutylaluminoxane (aged for three months at ambient temperature, and indicated by IR to contain no detectable amount of hydroxyl groups), hardly reacted with rac-dimethylsilylbis(2-methylindenyl) zirconium dimethyl even at a higher Al/Zr ratio of 50. See FIG. 5, middle. Although the metallocene reacts with the tetraisobutyldialuminoxane (TIBAO) (formed using a water/Al ratio of 0.50 and used at an Al/Zr ratio of 5000), little bathochromic shift occurred, indicating formation of virtually no active catalyst formation. See FIG. 5, bottom. This observation of lack of formation of active catalyst was confirmed by the polymerization run described in Comparative Example G, below.

The following examples (Examples 11–14 and Comparative Examples A–G) illustrate the highly advantageous results achievable using the polymerization reactions of this invention.

EXAMPLE 11

The hydroxy IBAO used in this run had 6.16. wt % Al and had been stored in a freezer at −10° C. in drybox for six days. The IR spectrum showed an absorbance of 0.458 for the 3623 $cm^{-1}$ OH band, roughly 4.2 OH per 100 Al atoms.

Polymerization of propylene was carried out in a 2-L stainless steel oil-jacketed reactor which had previously been heated to 100° C. under vacuum for one hour. After the reactor was charged with purified toluene (600 mL) and propylene (400 mL), a 2-mL solution of 1% TIBA in hexane was injected into the reactor and the mixture was stirred at 50° C. for 5 minutes.

After that polymerization was initiated by injecting a catalyst solution of rac-dimethylsilylbis(2-methylindenyl) zirconium dimethyl (2 µmol) and hydroxy IBAO (50 µmol, Al/Zr=25) in 3 mL of toluene which had previously been allowed to stand at ambient temperature for one hour. The mixture was stirred at 800 rpm. The temperature immediately began to rise from 50° C. to peak at 74° C. 9 minutes later. No make-up propylene was added. After ten minutes of reaction, the unreacted propylene was quickly vented to stop the polymerization. After adding methanol (>1000 mL), filtering, and drying the solids under vacuum at 100° C. overnight, 101 g of isotactic polypropylene was isolated; polymer properties: M.P. (onset of second melt):

146.3° C.; Melt Flow Index (MFI) (230/5): 40.68 (g/10 min); mmmm %: 93.9%; Isotactic Index: 97.3%

EXAMPLE 12

This polymerization of propylene used an IBAO with roughly 4.0 OH groups per 100 Al atoms. The materials and procedure were as in Example 11 except that an Al/Zr ratio of 50 and more toluene (800 mL) were used. Yield: 127 g; M.P.(onset of second melt):

144.9° C.; MFI (230/5): 87.97 (g/10 min); mmmm %: 93.1%; Isotactic Index: 97.4%.

EXAMPLE 13

This IBAO used in this polymerization contained approximately 3.2 OH groups per 100 Al atoms. The materials and procedure were as in Example 11 except that an Al/Zr ratio of 30, and more toluene (800 mL) were used. Yield: 88.6 g.; M.P.(onset of second melt): 146.9° C.; MFI (230/5): 56.28 (g/10 min); mmmm %: 93.1%; Isotactic Index: 96.9%.

COMPARATIVE EXAMPLE A

The procedure of Example 11 was repeated, except that the catalyst solution was rac-dimethylsilylbis(2-methylindenyl)zirconium dimethyl (1.0 µmol) and conventional methylaluminoxane (MAO) (1.0 mmol, Al/Zr=1000) in toluene, and no TIBA was used as scavenger. Compared to Example 11, this propylene polymerization reaction was much less exothermic, taking a whole hour of reaction for temperature to rise from 50° C. to 81° C.; Yield: 146 g; M.P.(onset of second melt): 144.4° C.; MFI (230/5): 79.90 (g/10 min); mmmm %: 92.2%; Isotactic Index: 96.5%.

COMPARATIVE EXAMPLE B

This polymerization was carried out in a 300-mL Parr reactor equipped with an internal cooling coil. Into the reactor in drybox was charged with a catalyst solution of rac-dimethylsilylbis(2-methylindenyl)zirconium dimethyl (0.3 µmol) and MAO (1.5 mmol, Al/Zr=5000) in about 150 mL of dry toluene. The reactor was sealed, transferred, and heated to 68° C. With stirring set at 800 rpm, the polymerization was initiated by pressing in 28 g of liquid propylene. The temperature was maintained at 70° C. by applying cooling intermittently. After 10 minutes, the polymerization was quenched by adding MeOH. Yield: 7.2 g. M.P.(onset of second melt): 145.9° C.

COMPARATIVE EXAMPLE C

The procedure was as in Example 11 except that the catalyst solution was rac-dimethylsilylbis(2-methylindenyl) zirconium dimethyl (1.0 µmol) and MAO (0.1 mmol, Al/Zr= 100) in toluene. No exothermic reaction was observed. The reaction after one hour produced only a trace of solid polymer.

COMPARATIVE EXAMPLE D

This polymerization used TIBAO (tetraisobutylaluminoxane) made by hydrolyzing TIBA with a half equivalent of water (water to aluminum ratio=0.5) and the IR spectrum of the product showed no evidence of any OH group present. The procedure was as in Example 11 except that an Al/Zr ratio of 100 was used. No polymerization activity was observed.

COMPARATIVE EXAMPLE E

This polymerization was carried out in a 300-mL Parr reactor with procedure analogous to that in Comparative Example D except that the Al/Zr ratio was 5000, reaction temperature was 70° C., and reaction time was 20 minutes. Only 0.91 g of polymer was isolated.

COMPARATIVE EXAMPLE F

This polymerization used hydroxyisobutylaluminoxane having approximately 5.3 OH groups per 100 Al atoms. The procedure was as in Example 11 except that an Al/Zr ratio of 3000 was used. The polymerization was initially as exothermic as that in Example 11. However, when the temperature reached 63° C. (from 50° C.) after 4 minutes of reaction, the exothermic reaction suddenly ceased and the temperature quickly reversed its rising trend, returning to 52° C. in the next 6 minutes. The reaction was allowed to continue for an additional 20 minutes. Yield: 38.6 g. M.P. (onset of second melt): 148.0° C.; MFI (230/5): 16.67 (g/10 min); mmmm %: 92.6%; Isotactic Index: 96.8%

COMPARATIVE EXAMPLE G

This polymerization used hydroxyisobutylaluminoxane having approximately 3.8 OH groups per 100 Al atoms. The procedure was as in Example 11 except that the metallocene used was rac-diethylsilylbis(2-methylindenyl)zirconilum dichloride not the dimethyl analog. In addition, an Al/Zr ratio of 50, and more toluene (800 mL) wer e used. No reaction was observed.

EXAMPLE 14

This ethylene polymerization used hydroxyisobutylaluminoxane made by hydrolyzing TIBA with 0.9 equivalent of water and with approximately 1.5 OH groups per 100 Al atoms at the time of use. The procedure was as in Example 11 with the following modifications: The catalyst used was a mixture of bis(1-butyl-3-methylcyclopentadienyl)zirconium dimethyl (2 $\mu$mol) and hydroxyisobutylaluminoxane (200 $\mu$mol), and was allowed to stand at ambient temperature for one hour before being injected. The reactor was charged with 900 mL of dry toluene and pressurized with 300 psig of ethylene, which was fed as needed during polymerization to maintain the pressure. Polyethylene yield: 55.0 g. M.P.(onset of first melt): 131.8° C. An attempt to determine melt flow index (MFI) failed because the polymer would not move through the orifice (i.e., the polymer had an extremely low MFI), indicative of a very high molecular weight polyethylene.

While this invention has been specifically illustrated by reactions between a metallocene and a hydroxyaluminoxane, it is to be understood that other suitable organometallic reactants having an appropriate leaving group can be employed. For example it is contemplated that the organometallic complexes described in the following publications will form ionic compounds of this invention, provided that at least one of the halogen atoms bonded to the d-block or f-block metal atom is replaced by a suitable leaving group such as a methyl, benzyl, or trimethylsilylmethyl group:

Small, B. L.; Brookhart, M.; Bennett, A, M. A. *J. Am. Chem. Soc.* 1998, 120, 4049.

Small, B. L.; Brookhart, M. *J. Am. Chem. Soc.* 1998, 120 7143.

Johnson, L. K.; Killian, C. M.; Brookhart, M. *J. Am. Chem. Soc.* 1995, 117, 6414.

Killian, C. M.; Johnson, L. K.; Brookhart, M. *Organometallics* 1997, 16, 2005.

Killian, C. M.; Tempel, D. J.; Johnson, L. K.; Brookhart, M. *J. Am. Chem. Soc.* 1996, 118, 11664.

Johnson, L. K.; Mecking, S.; Brookhart, M. *J. Am. Chem. Soc.* 1996, 118, 267.

The materials referred to by chemical name or formula anywhere in the specification or claims hereof are identified as ingredients to be brought together in connection with performing a desired operation or in forming a mixture to be used in conducting a desired operation. Accordingly, even though the claims hereinafter may refer to substances in the present tense ("comprises", "is", etc.), the reference is to the substance, as it existed at the time just before it was first contacted, blended or mixed with one or more other substances in accordance with the present disclosure. The fact that a substance may lose its original identity through a chemical reaction, complex formation, salvation, ionization, or other transformation during the course of contacting, blending or mixing operations, if done in accordance with the disclosure hereof and with the use of ordinary skill of a chemist and common sense, is within the purview and scope of this invention.

Each and every patent or other publication referred to in any portion of this specification is incorporated in full into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A compound which comprises a cation derived from d-block or f-block metal compound by loss of a leaving group and an aluminoxate anion derived by transfer of a proton from a stable or metastable hydroxyaluminoxane to said leaving group.

2. A compound according to claim 1 wherein the metal of said metal compound is a metal of Group 4.

3. A compound according to claim 1 wherein the leaving group is a hydrocarbyl group bonded directly to said d-block or f-block metal compound.

4. A compound according to claim 1 wherein the leaving group is a methyl group bonded directly to said d-block or f-block metal compound.

5. A compound according to claim 4 wherein the metal of said metal compound is a metal of Group 4.

6. A compound according to claim 1 wherein the aluminoxate anion is derived from said hydroxyaluminoxane functioning as a Brønsted acid.

7. A compound according to claim 1 wherein said hydroxyaluminoxane before said proton transfer has a ratio of less than one hydroxyl group per aluminum atom.

8. A compound according to claim 1 wherein the hydroxyaluminoxane prior to said transfer is an akylaluminoxane in which at least one aluminum atom has a hydroxyl group bonded thereto, and in which the alkyl groups each contain at least two carbon atoms.

9. A compound according to claim 8 wherein the alkyl groups are isobutyl groups.

10. A compound according to claim 9 wherein the metal of said metal compound is zirconium.

11. A compound according to claim 1 wherein said metal compound prior to said transfer is a metallocene.

12. A compound according to claim 1 wherein prior to said transfer, said compound has at least two leaving groups bonded to said d-block or f-block metal.

13. A compound according to claim 1 wherein prior to said transfer, said compound has a single leaving group bonded at two different sites to said d-block or f-block metal.

14. A compound according to claim 1 wherein prior to said transfer said compound is rac-dimethylsilylbis(2-methylindenyl)zirconium dimethyl.

15. A compound according to claim 1 wherein prior to said transfer said compound is bis(1-butyl-3-methylcyclopentadienyl)zirconium dimethyl.

16. A compound according to claim 14 wherein prior to said transfer said hydroxyaluminoxane is an isobutylaluminoxane in which at least one aluminum atom has a hydroxyl group bonded thereto.

17. A compound according to claim 15 wherein prior to said transfer said hydroxyaluminoxane is an isobutylaluminoxane in which at least one aluminum atom has a hydroxyl group bonded thereto.

18. A compound which comprises (i) a cation derived from a d-block or f-block metal compound by loss of a leaving group, and (ii) an aluminoxate anion devoid of said leaving group.

19. A compound which comprises (i) a cation derived from a d-block or f-block metal compound by loss of a leaving group transformed into a neutral hydrocarbon, and (ii) an aluminoxate anion derived by loss of a proton from a hydroxyaluminoxane having, prior to said loss, at least one aluminum atom having a hydroxyl group bonded thereto.

20. A process which comprises contacting a d-block or f-block metal compound having at least leaving groups with a hydroxyaluminoxane in which at least one aluminum atom has a hydroxyl group bonded thereto so that one of said leaving groups is lost.

21. A process according to claim 20 wherein one of said leaving groups is lost in the form of a hydrocarbon.

22. A process according to claim 20 wherein the metal of said metal compound is a metal of Group 4.

23. A process according to claim 20 wherein at least one of said leaving groups is a hydrocarbyl group bonded directly to said d-block or f-block metal compound.

24. A process according to claim 20 wherein the leaving group that is lost is a methyl group bonded directly to said d-block or f-block metal compound.

25. A process according to claim 24 wherein the metal of said metal compound is a metal of Group 4.

26. A process according to claim 20 wherein said hydroxyaluminoxane is transformed into an aluminoxate anion by functioning as a Brønsted acid.

27. A process according to claim 26 wherein said hydroxyaluminoxane before said transformation has a ratio of less than one hydroxyl group per aluminum atom.

28. A process according to claim 20 wherein the hydroxyaluminoxane is an alkylaluminoxane in which at least one aluminum atom has a hydroxyl group bonded thereto, and in which the alkyl groups each contain at least two carbon atoms.

29. A process according to claim 28 wherein the alkyl groups are isobutyl groups.

30. A process according to claim 29 wherein the metal of said metal compound is zirconium.

31. A process according to claim 20 wherein said metal compound prior to said contact is a metallocene.

32. A process according to claim 20 wherein prior to said contact said compound is rac-dimethylsilylbis(2-methylindenyl)zirconium dimethyl.

33. A process according to claim 20 wherein prior to said contact said compound is bis(1-butyl-3-methylcyclopentadienyl)zirconium dimethyl.

34. A process according to claim 32 wherein prior to said contact said hydroxyaluminoxane is an isobutylaluminoxane in which at least one aluminum atom has a hydroxyl group bonded thereto.

35. A process according to claim 33 wherein prior to said contact said hydroxyaluminoxane is an isobutylaluminoxane in which at least one aluminum atom has a hydroxyl group bonded thereto.

36. A process which comprises donating a proton from an aluminoxane to a leaving group of a d-block or f-block metal compound to form a compound composed of a cation derived from said metal compound and an aluminoxate anion devoid of said leaving group.

37. A process which comprises interacting a d-block or f-block metal compound having two leaving groups and a hydroxyaluminoxane having at least one aluminum atom that has a hydroxyl group bonded thereto to form a compound composed of a cation through loss of a leaving group which is transformed into a neutral hydrocarbon, and an aluminoxate anion derived by loss of a proton from said hydroxyaluminoxane.

38. A process according to claim 37 wherein prior to said interaction, said d-block or f-block metal compound has at least two leaving groups bonded to said d-block or f-block metal.

39. A process according to claim 37 wherein prior to said interaction, said compound has a single leaving group bonded at two different sites to said d-block or f-block metal.

* * * * *